US006804654B2

(12) United States Patent
Kobylevsky et al.

(10) Patent No.: US 6,804,654 B2
(45) Date of Patent: Oct. 12, 2004

(54) SYSTEM AND METHOD FOR PROVIDING PRESCRIPTION SERVICES USING VOICE RECOGNITION

(75) Inventors: Paul Kobylevsky, Flushing, NY (US); Valery Gurovich, Ramsey, NJ (US)

(73) Assignee: Telemanager Technologies, Inc., Newark, NJ (US)

( * ) Notice: Subject to any disclaimer, the term of this patent is extended or adjusted under 35 U.S.C. 154(b) by 0 days.

(21) Appl. No.: 10/073,645

(22) Filed: Feb. 11, 2002

(65) Prior Publication Data

US 2003/0154083 A1 Aug. 14, 2003

(51) Int. Cl.[7] .............................................. G10L 15/00
(52) U.S. Cl. .................................... 704/275; 704/270.1
(58) Field of Search .............................. 704/270, 270.1, 704/275; 600/300; 379/88, 22; 705/2

(56) References Cited

U.S. PATENT DOCUMENTS

| | | | | | |
|---|---|---|---|---|---|
| 5,772,585 | A | * | 6/1998 | Lavin et al. ................. | 600/300 |
| 6,088,429 | A | * | 7/2000 | Garcia ...................... | 379/88.22 |
| 6,108,634 | A | * | 8/2000 | Podnar et al. ................ | 705/2 |
| 6,314,402 | B1 | * | 11/2001 | Monaco et al. ............. | 704/275 |

OTHER PUBLICATIONS

Chopra et al., Voice Activated Networked Workstation for a Physically Disabled Physician, Proceedings of the 16th Annual International Conference of the IEEE, Nov. 3–6, 1994, pp. 478–479.*

* cited by examiner

Primary Examiner—David D. Knepper
(74) Attorney, Agent, or Firm—Wolff & Samson PC

(57) ABSTRACT

An automated prescription transcription and dispatch service using voice recognition and a customizable, user-friendly telephony interface is provided. A doctor or other medical personnel can call a prescription services system, and provide spoken prescription information. The call can be placed directly to the prescription services system using the Public Switched Telephone Network (PSTN) or Voice-over-IP (VoIP) connection, or can be forwarded to the prescription services system from a telephone number corresponding to a pharmacy. The system prompts the user through audible menus to provide prescription and patient information. The spoken information is digitized, recorded, and stored in the prescription services system, and then transcribed into textual format. The transcribed prescriptions are then transmitted to the doctor or medical personnel via variety of communication methodologies, such as fax, e-mail, XML, and electronic data interchange, for confirmation, review, and record keeping purposes. Further, the transcribed prescriptions are transmitted to a pharmacy, using similar communication methodologies, for review and further processing. The caller can call the prescription services system to review the spoken and transcribed prescription information stored from a previous session. The prescription services system can be integrated into existing pharmacy management systems using electronic data interchange (EDI) and other data exchange protocols.

55 Claims, 6 Drawing Sheets

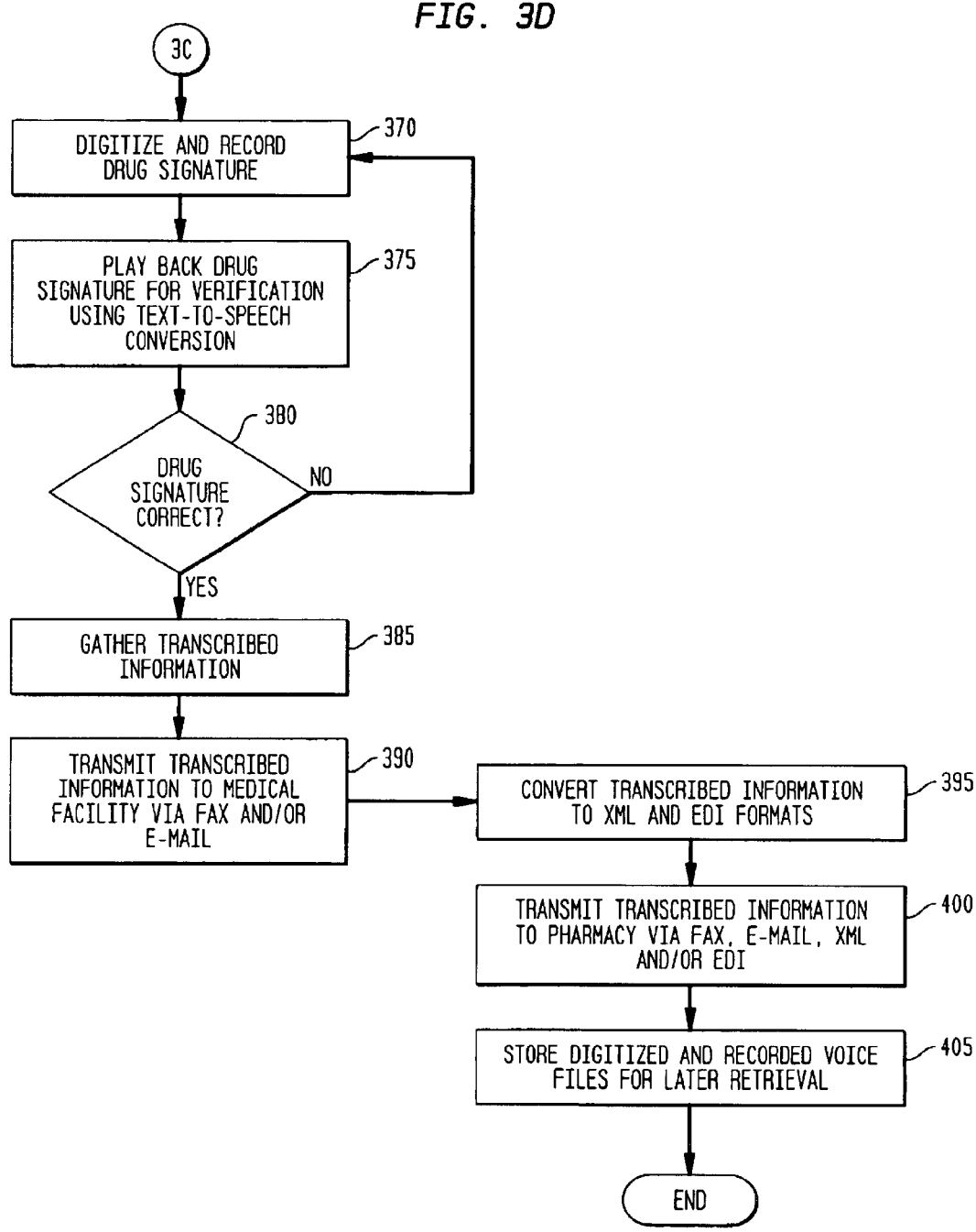

SYSTEM AND METHOD FOR PROVIDING PRESCRIPTION SERVICES USING VOICE RECOGNITION

BACKGROUND OF THE INVENTION

1. Field of the Invention

The present invention relates to a method and apparatus for providing prescription services. More specifically, the invention relates to a method and apparatus for providing prescription, prescription refill, transcription, and forwarding services using voice recognition software and associated computer hardware.

2. Related Art

In the medical profession, doctors and other medical personnel frequently prescribe drugs and other medicines for their patients. Traditionally, such prescriptions are recorded by the doctor on paper, and are given to the patient for filling at a local pharmacy. Additionally, doctors frequently call pharmacies to place prescriptions, which may later be picked up by the patient. Both written and telephonic prescriptions require the prescribing doctor or the pharmacy to write down prescription information, thereby delaying the refill process and requiring time and effort on the part of such personnel. Further, the refill process is hindered by transcription errors that may occur when pharmacy personnel transcribe a doctor's telephoned prescription, or when the pharmacist is required to read a doctor's unintelligible handwriting. Finally, when prescriptions are manually transcribed, there is no efficient way for a doctor to review a prescription once it has been recorded by the pharmacy.

Accordingly, it would be desirable to provide a system for receiving prescriptions from a caller over a telephone, transcribing same, and transmitting textual prescription information to pharmacies. Further, it would be desirable to provide a system for transmitting confirmation information to a doctor or medical facility, and which allows the caller to quickly and efficiently review prescription information.

OBJECTS AND SUMMARY OF THE INVENTION

It is an object of the present invention to provide a method and apparatus having voice recognition capabilities for receiving, transcribing, and forwarding prescriptions to pharmacies for filling.

It is an additional object of the present invention to provide a method and apparatus wherein prescriptions can be received from a doctor or medical personnel over a telephone and using voice recognition techniques, the prescription being transcribed and transmitted to a pharmacy for filling.

It is a further object of the present invention to provide a method and apparatus wherein prescriptions can be transcribed and transmitted back to a doctor or medical facility for confirmation or review prior to transmission to a pharmacy for filling.

It is still another object of the present invention to provide a method and apparatus wherein prescriptions can be stored centrally or locally, and later retrieved.

It is a further object of the present invention to provide a method and apparatus wherein a caller can be prompted to provide prescription information through customized, audible menus that can be accessed by a telephone.

It is still another object of the present invention to provide a voice recognition prescription services system that can be customized to include a variety of audible prompts.

It is a further object of the present invention to provide a voice recognition prescription services system that can receive prescriptions from telephone calls from doctors.

It is yet another object of the present invention to provide a prescription services system that can receive prescriptions forwarded from a pharmacy telephone number, unbeknownst to a caller.

The present invention relates to a method and apparatus for providing prescription services using voice recognition. Doctors or other medical personnel can call a voice recognition prescription services system using a standard telephonic connection. The prescription services system prompts the caller to provide prescription information using a variety of customizable, user-friendly, and audible prompts and menus. The doctor can call the prescription services system directly, or can call a pharmacy telephone number, wherein the call can then be forwarded, unbeknownst to the caller, to the prescription services system. The caller can provide spoken prescription information, and can review, confirm, and edit the information provided prior to or after transcription. Once the prescription information has been provided by the caller, the prescription services system transcribes the prescription information into a textual format using voice recognition procedures. Both the voice prescription information and the transcribed prescriptions can be stored in the prescription system for later retrieval and review by the caller. The transcribed prescriptions can then be sent to the pharmacy for processing. Additionally, the transcribed prescriptions can be sent to the doctor or medical facility for confirmation, review, and record keeping purposes.

BRIEF DESCRIPTION OF THE DRAWINGS

Other important objects and features of the invention will be apparent from the following Detailed Description of the Invention taken in connection with the accompanying drawings in which:

FIGS. 3a–3d are flowcharts showing processing logic of the present invention.

DETAILED DESCRIPTION OF THE INVENTION

The present invention relates to a method and apparatus for providing prescription services using voice recognition. Doctors and other medical personnel can call the system using a standard telephonic connection. The system can prompt the caller with a variety of customized, user-friendly prompts and menus to provide prescription information. The system transcribes and stores the prescription information using voice recognition procedures. The transcribed prescriptions can then be sent to a pharmacy for filling, and to the doctor or medical facility for confirmation, record keeping, and review purposes.

Figure 1:
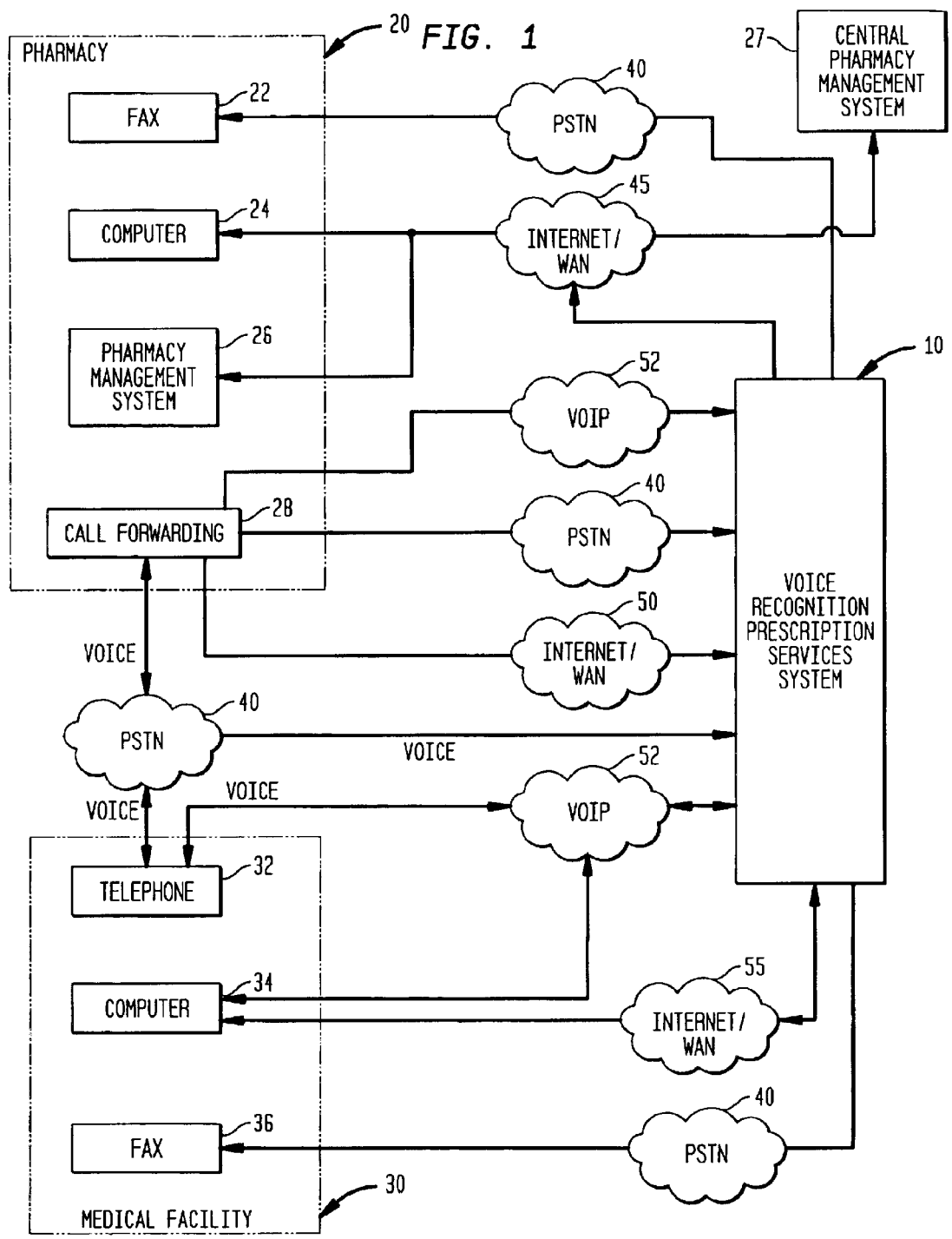
FIG. 1 is schematic showing the system of the present invention implemented between a medical facility and a pharmacy.

FIG. 1 is a schematic diagram showing the prescription services system 10 of the present invention, illustratively implemented between a pharmacy 20 and a medical facility 30. The prescription services system 10 can communicate with a number of pharmacies, doctors, and medical facilities using a variety of communications systems known in the art, such as Public Switched Telephone Network (PSTN) connections, Wide Area Network (WAN) connections, and various Internet connection methodologies (e.g., frame relay, T1, T3, ISDN, dial-up, xDSL, and cable modem).

Medical facility 30 can be any doctor's office, hospital, or other facility where medical services and prescriptions are typically prescribed. When a doctor or other medical personnel wishes to prescribe a medicine for a given patient, he or she can use telephone 32 to dial a prescription telephone number. Upon dialing the prescription telephone number, a voice connection is made between telephone 32 and the prescription services system 10 via the PSTN 40. Alternatively, a telephonic connection can be established between telephone 32 or computer 34 and the prescription services system 10 using a Voice Over Internet Protocol ("VoIP") connection 52. It is to be understood that VoIP connection 52 can be established using any VoIP technology known in the art. Likewise, communication can be established between computer 34 and the prescription services system 10 by means of Internet/WAN connection 55.

A variety of prescription telephone numbers can be provided for medical personnel to use. In a first embodiment, the caller can dial a prescription telephone number that connects directly to prescription services system 10. In this case, a voice connection is established directly from telephone 32 to prescription services system 10 via PSTN 40 or VoIP connection 52. In a second embodiment, the caller can dial a prescription telephone number corresponding to a pharmacy. The call can then be forwarded, unbeknownst to either the caller or the pharmacy, to the prescription services system 10. Thus, according to this methodology, a connection can be established between telephone 32 and the prescription services system 10 via call forwarding system 28 and PSTN 40. Alternatively, Internet/WAN connection 50 or VoIP connection 52 could be utilized. Call forwarding system 28 can be located at either the pharmacy 20, or some other location, such as a telephone company facility (e.g., a telephone company central office).

Using either the direct voice PSTN or VoIP connection, or the voice-forwarded PSTN or VoIP connection, a call originating from telephone 32 in medical facility 30 or a doctor's office is received by prescription services system 10 via either PSTN connection 40, Internet/WAN connection 50, or VoIP connection 52. Prescription services system 10 prompts the caller to provide prescription information, and transcribes same into a human and/or computer readable form (i.e., ASCII text file, HTML, XML, EDI, or other format) for later transmission to pharmacy 20 for filling and medical facility 30 for confirmation, review, and record keeping. Additionally, prescription service system 10 records the voice prescription information and stores same for later retrieval and review by a doctor, pharmacist, or other medical personnel.

When the voice prescription information has been stored and transcribed by prescription services system 10, transcribed prescription information can be sent to pharmacy 20 for filling. A variety of connection methodologies allow prescription services system 10 to communicate with pharmacy 20 for the purpose of exchanging prescription information and other data. For example, prescription services system 10 can transmit the transcribed prescriptions to a fax machine 22 located at pharmacy 20. Upon receipt of the faxed prescription, a pharmacist can then process the prescription. Additionally, prescription services system 10 can exchange prescription information with a computer 24 and/or a pharmacy management system 26 located at the pharmacy 20 via Internet/WAN connection 45. Prescription services system 10 can transmit the prescription information to computer 24 as an e-mail message, Hypertext Markup Language (HTML) page, Extensible Markup Language (XML) page, Electronic Data Interchange (EDI) message, or other data format, sent via Internet/WAN connection 45. Optionally, the prescriptions services system 10 can transmit the transcribed prescriptions to a central pharmacy management system 27, located external to pharmacy 20. Thus, the prescription services system 10 can operate with pharmacy management systems located within a pharmacy or external to same.

Pharmacy management system 26, central pharmacy management system 27, and users thereof can also interact with and exchange prescription information with prescription services system 10 using Internet/WAN connection 45. Pharmacy management system 26 and central pharmacy management system 27 can be any proprietary or legacy pharmacy management systems known in the art which are capable of receiving prescription information. Further, pharmacy management system 26, central pharmacy management system 27, and computer 24 can allow a pharmacist to manipulate prescription information stored on prescription services system 10, or downloaded to the pharmacy via Internet/WAN connection 45.

A pharmacist can customize prompt information provided to callers by prescription services system 10 using computer 24, pharmacy management system 26, or by calling prescription service system 10 through a standard voice PSTN or VoIP connection. For example, a customized greeting identifying the pharmacy could be provided by the pharmacist and recorded by prescription services system 10, or a sequence of menu prompts and call flow could be customized by the pharmacist or other individual. Importantly, the transcription services provided by prescription services system 10 allow the pharmacy 20 to quickly and efficiently receive transcribed prescriptions without having to engage in the transcription process. Such an advantage provides an added degree of accuracy for the prescription refill process by obviating the need for human transcription and eliminating the influence of human error.

In addition to providing prescription information to pharmacy 20, prescription services system 10 can provide confirmation information to medical facility 30. Such information can be used by a doctor or other medical personnel for record keeping, confirmation, and review purposes. When the voice prescription information has been transcribed and stored by prescription services system 10, the transcribed prescription can be sent to the medical facility 30 as a fax, e-mail, or digital transmission. For example, a confirmatory fax can be sent to fax machine 36 residing at medical facility 30 via PSTN 40. Further, a confirmatory message can be sent to computer 34 at medical facility 30 via an e-mail message, Hypertext Markup Language (HTML) page, Extensible Markup Language (XML) page, Electronic Data Interchange (EDI) message, or other data format, transmitted through Internet/WAN connection 55. Additionally, computer 34 can function as a networked node that is connected to prescription service system 10 via Internet/WAN connection 55. Thus, using computer 34, a doctor can review the contents and/or status of transcribed prescription information on prescription services system 10. It is to be understood that other connection methodologies known in the art can be used to exchange prescription information between prescription services system 10, pharmacy 20, and medical facility 30. Further, in an additional embodiment of the present invention, a caller can review, confirm, and edit spoken prescription information provided to prescription services system 10 prior to transcription of same.

Figure 2:
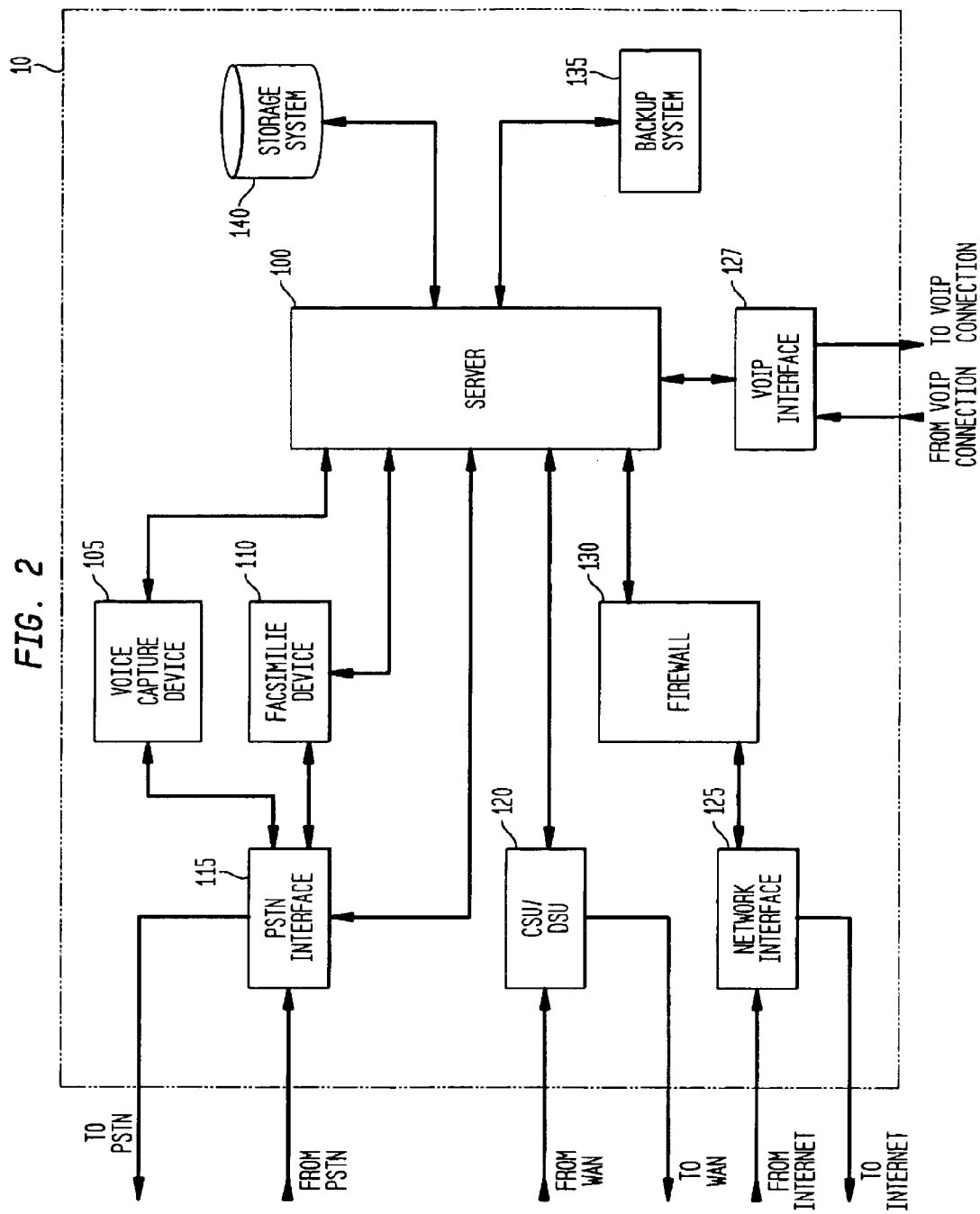
FIG. 2 is a schematic showing the voice recognition prescription services system of the present invention in greater detail.

FIG. 2 is a schematic diagram showing various component parts of prescription services system 10 in greater detail. Voice phone calls from doctors can be received by the system, and outgoing transcribed prescription information can be sent from the system. Further, information stored in the system can be exchanged with and/or monitored by pharmacies, doctors, and other medical personnel through digital communication links. As shown in the figure, information can be received by and transmitted from prescription services system 10 by PSTN, WAN, VoIP, or Internet connections. It is to be understood that other communication methodologies are considered within the scope of the present invention.

Prescription services system 10 may comprise a variety of interfaces for external communication, such as PSTN interface 115, Channel Service Unit/Data Service Unit (CSU/DSU) 120, network interface 125, and VoIP interface 127. PSTN interface 115 allows the prescription services system 10 to receive voice calls and transmit fax messages. CSU/DSU 120 allows prescription services system 10 to be connected to a WAN, such as a medical facility WAN or a pharmacy WAN. It is to be understood that CSU/DSU 120 can be any WAN connection device known in the art and suitable for various connection methodologies, such as frame relay, T1, T3, and xDSL. Network interface 125 allows prescription services system 10 to be connected to a public network, such as the Internet, for receiving and transmitting prescription information. Specifically, network interface 125 allows transcribed prescriptions to be sent via e-mail to a pharmacy and/or medical facility. Firewall 130, connected to network interface 125, can optionally filter traffic transmitted from and received by the prescription services system 10. VoIP interface 127 allows voice over IP connections to be established between a caller and prescription services system 10, using any VoIP technology known in the art.

Importantly, server 100 can contain the control logic and procedures of the present invention that allow voice prescription information to be acquired from callers, stored, managed, transcribed, and submitted to pharmacies and medical facilities for processing, review, confirmation, and record keeping. Server 100 can be any server known in the art, such as one having an Intel® microprocessor manufactured by Intel Corporation, or a SPARC® microprocessor manufactured by Sun Microsystems, Inc. Preferably, server 100 has sufficient memory and storage capacity to allow a plurality of incoming and outgoing voice and transcribed prescriptions to be handled simultaneously. Storage system 140, connected to server 100, allows for the quick storage and retrieval of prescription information and system logic. Storage system 140 can be any disk or other memory storage system known in the art such as a RAID (Redundant Array of Inexpensive Disks) array system. Backup system 135 allows information processed by server 100 and storage system 140 to be periodically backed up to storage media such as disks or tapes. Further, storage system 140 can serve as a mirroring system to provide fault tolerance.

When voice telephone calls are received by PSTN interface 115, they are processed by voice capture device 105. Voice capture device 105 provides digitization services that allow server 100 to process human speech and perform transcription operations. Further, voice capture device 105 can provide voice synthesis capabilities, so that server 100 can communicate with and respond to a caller using speech synthesis. Such capability may be provided by pre-recorded, digitized prompts, or other voice synthesis techniques known in the art, or a combination thereof.

When server 100 acquires prescription information from a caller via PSTN interface 115 and voice capture device 105, the acquired, digitized voice prescription information is stored in storage subsystem 140, where it can later be retrieved and reviewed by the caller. Once the call is complete, server 100 processes the digitized voice prescription information and transcribes same to provide a textual version of the prescription. The text prescription is then transmitted to a pharmacy for further processing and to a medical facility for confirmation, via fax using PSTN interface 115 or digital transmission using network interface 125 or CSU/DSU 120. Further, network interface 125 and CSU/DSU 120 allow the pharmacy and/or the medical institution to remotely interact with and manage information stored by server 100.

FIGS. 3a–3d are flowcharts showing processing logic of the present invention. Such logic can be embodied as computer software residing in server 100 and storage system 140 of the present invention. The processes disclosed herein allow a caller to provide voice prescription information to the prescription services system of the present invention through user-friendly, audible prompts and menus, review the prescription information provided, and have the voice prescription information transcribed and transmitted to both a pharmacy and a medical institution for further processing, confirmation, and record keeping. Further, the processing steps disclosed herein are illustrative in nature, and can be varied in accordance with the desires of the user.

Figure 3A:
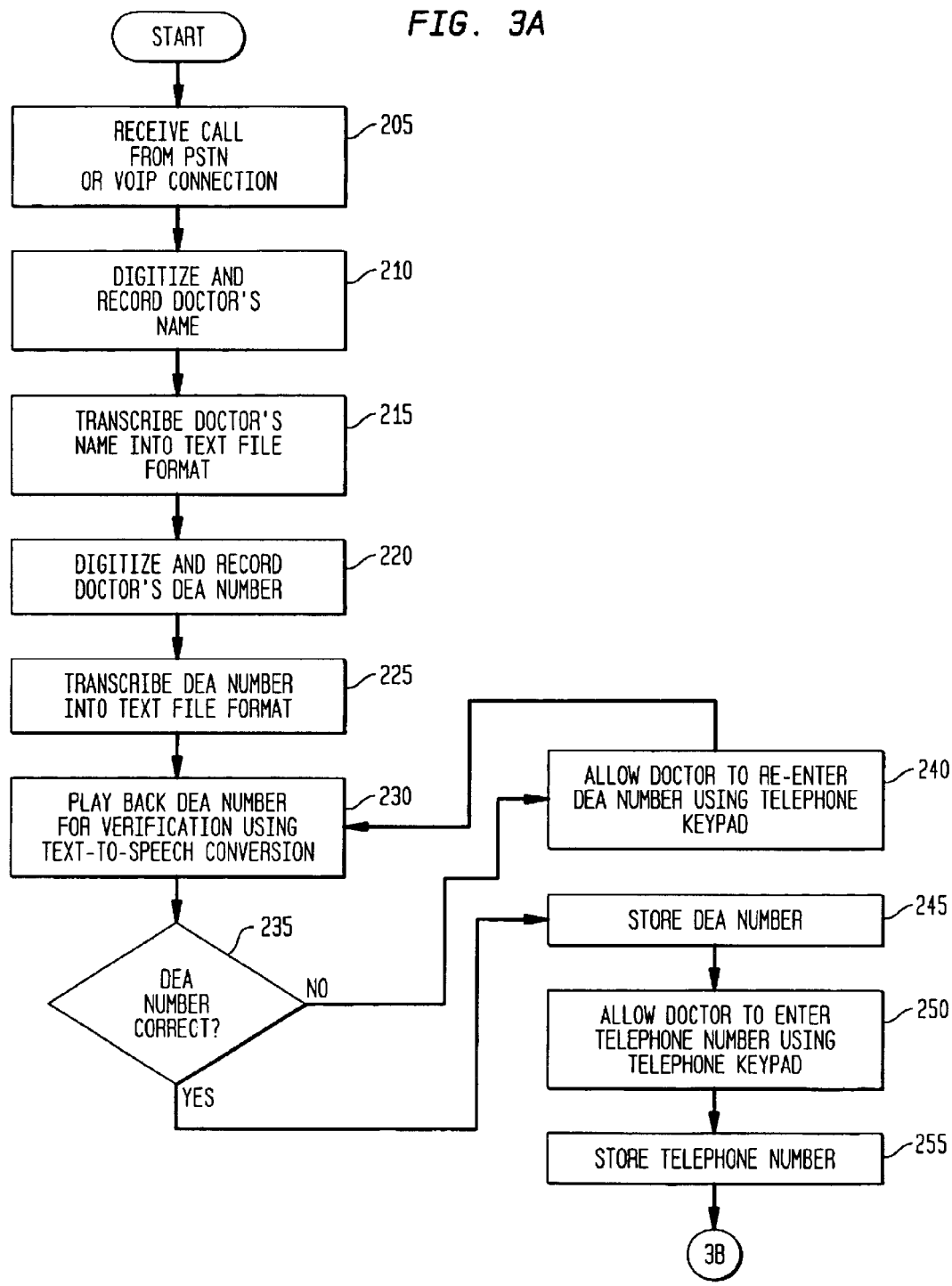

FIG. 3a is a flowchart showing initial processing logic of the present invention. Beginning in step 205, a telephone call originating from a doctor is received by the prescription services system via a PSTN or VoIP connection. The system then prompts the caller to speak his or her name. In step 210, the doctor's name is recorded and digitized. Further, the spoken name is converted to a digital format, and stored as a sound file, using sound formats known in the art (i.e., .WAV format, .MP3 format, or .AU format). When the spoken information is provided, the caller can review, confirm, or re-record his or her name. In step 215, the doctor's digitized name is transcribed into text format using speech-to-text conversion algorithms known in the art. Examples of such speech-to-text programs include systems manufactured by Nuance Communications, Inc.

Once transcribed, step 220 is invoked, wherein the caller is prompted to provide a Drug Enforcement Agency (DEA) number. The DEA number is then digitized, recorded, and stored in a sound file format known in the art (i.e., .WAV format). Step 220 then invokes step 225, wherein the recorded and digitized DEA number is transcribed into text format using known speech-to-text algorithms. Once transcribed, the DEA number is then played back to the caller in step 230 for verification purposes, using text-to-speech conversion and audio playback procedures. In step 235, the caller is prompted for an indication as to whether the DEA number is correct. If the caller indicates that the DEA number is incorrect, step 240 is invoked, wherein the caller can re-enter the DEA number using the numeric keypad of the telephone. Once the DEA number is re-entered, step 230 is re-invoked, and the re-entered DEA number re-played for verification.

In the event that the caller indicates in step 235 that the DEA number is correct, step 245 is invoked, wherein the DEA number is stored. Then, step 250 is invoked. In step 250, the caller is prompted to enter his or her telephone number using the keypad of the telephone. Optionally, the invention can be configured to play back the telephone number once it has been entered, allowing the caller to confirm and/or re-enter same. Once entered, the telephone number is stored in step 255. Processing then continues in FIG. 3b.

Figure 3B:
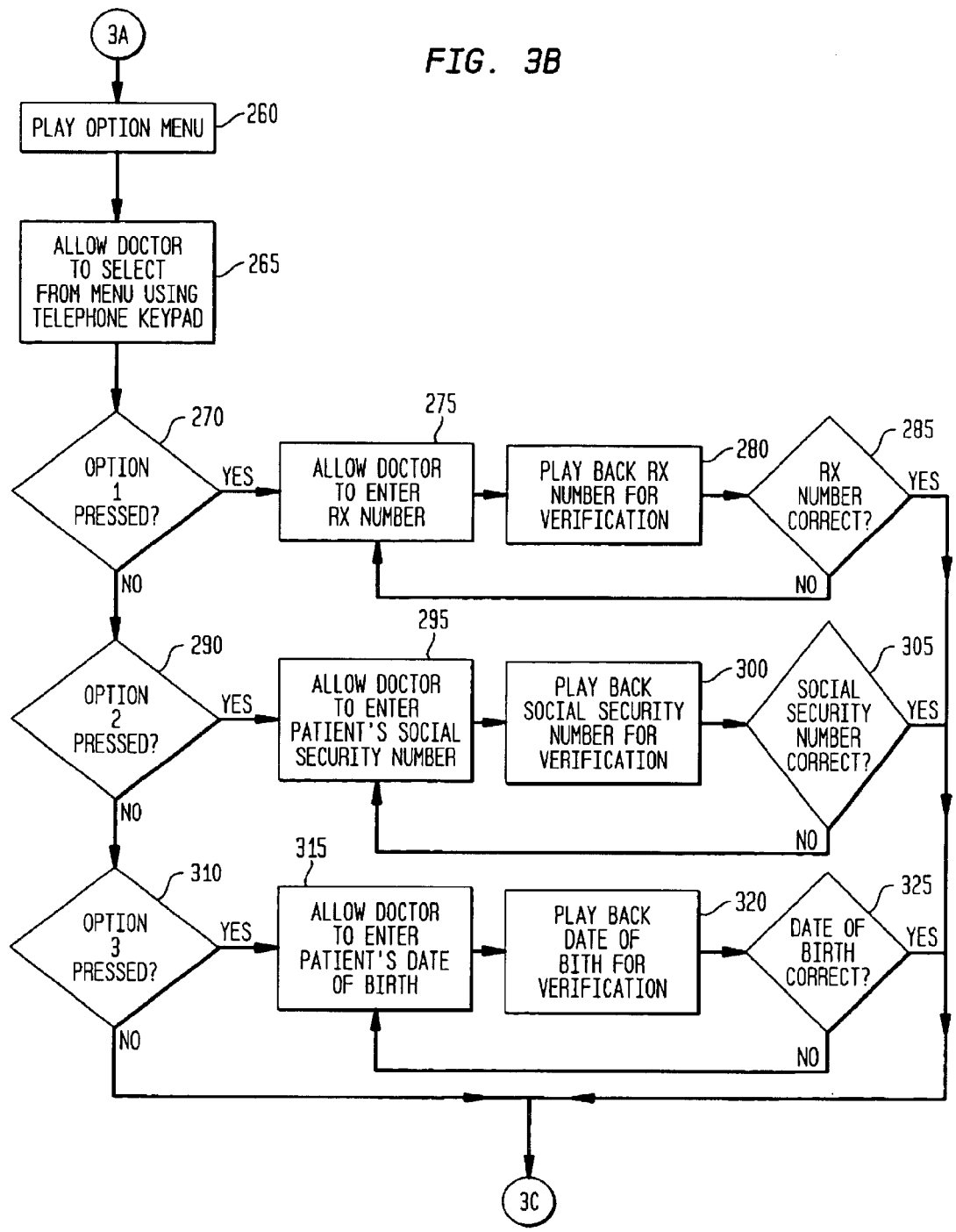

FIG. 3b is a flowchart showing additional processing steps of the present invention. Once preliminary information about the caller, such as a doctor's name, DEA number, and telephone number, has been acquired, processing then continues to step 260. In step 260, the caller is presented with an audible option menu. Such a menu is customizable according to a pharmacy's needs and/or desires, and is extendible to present the caller with a variety of information. In a preferred embodiment of the present invention, the audible option menu may be configured to recite the following line of speech: "If you know the patient's Rx number for refill authorization, press '1'; if you know the patient's Social Security Number, press '2'; if you know the patient's date of birth, press '3'; otherwise, press 9." Thus, a caller can identify a prescription for a patient using one or more known quantities of data. For example, if only the Rx number is known, the caller can provide same and associate a new prescription to a patient using the Rx number. Further, if only the patient's Social Security Number is known, a prescription can be recorded, transcribed, and associated with a patient based upon same. It is to be understood that additional option menus can be played in step 260 without departing from the spirit of the present invention.

When the audible option menu has been played, step 265 is invoked, wherein a caller is prompted to select from the menu using the telephone keypad. Alternatively, the caller can select from the audible menu by speaking the number corresponding to the desired menu option. Once the desired option has been selected, step 265 invokes step 270, wherein a decision point is reached. In step 270, a determination is made as to whether the first menu option, corresponding to Rx information, has been selected. If a positive determination is made, step 275 is invoked, wherein the caller is prompted to ender the Rx number for refill authorization, either by voice or using the telephone keypad. Once the Rx number has been entered, step 275 invokes step 280, wherein the Rx number is played back, using known text-to-speech procedures, for verification purposes. Then, in step 285, the caller is prompted to indicate whether the played back Rx number is correct. If a negative indication is made, step 285 re-invokes step 275, so that the Rx number can be re-entered and verified. If a positive indication is made, processing continues to FIG. 3c.

In the event that a negative determination is made in step 270, step 290 is invoked, wherein another determination is made as to whether a second menu option has been selected. If the second menu option, corresponding to a Social Security Number information, has been selected, step 290 invokes step 295. In step 295, the caller is prompted to enter a patient's Social Security Number using the telephone keypad or other data entry method. Once entered, processing continues to step 300, wherein the Social Security Number is read back to the caller for verification purposes. Then, in step 305, a determination is made as to whether the Social Security Number is correct. If the caller enters a negative indication, step 305 re-invokes step 295, so that the Social Security Number can be re-entered and verified. If a positive indication is made, processing continues in FIG. 3c.

In the event that a negative determination is made in step 290, step 310 is invoked, wherein another decision is made as to whether a third option from the audible option menu was selected. If so, step 315 is invoked, wherein the caller is prompted to enter a patient's date of birth using the telephone keypad or other input means. In a preferred embodiment, the caller can enter the date of birth by first entering two digits corresponding to the month of birth, followed by two digits corresponding to the day of birth, followed by four digits corresponding to the year of birth. Once the date of birth has been entered, step 320 is invoked, wherein the date entered is played back using text-to-speech conversion. In step 325, the caller is prompted to indicate whether the date is correct. If the caller inputs a negative indication, step 315 is re-invoked, so that the date can be re-entered and verified. If a positive indication is made, processing continues in FIG. 3c.

The foregoing description of the audible option menu is illustrative in nature, and is not intended to limit the scope thereof. It is conceivable that other menu options could be included. For example, an option "9" could be included, wherein if the caller does not desire to enter information recited in the audible option menu, he or she may skip the call flow process of the menu (i.e., exit the menu), and move directly to the processes described below for FIG. 3c.

Figure 3C:
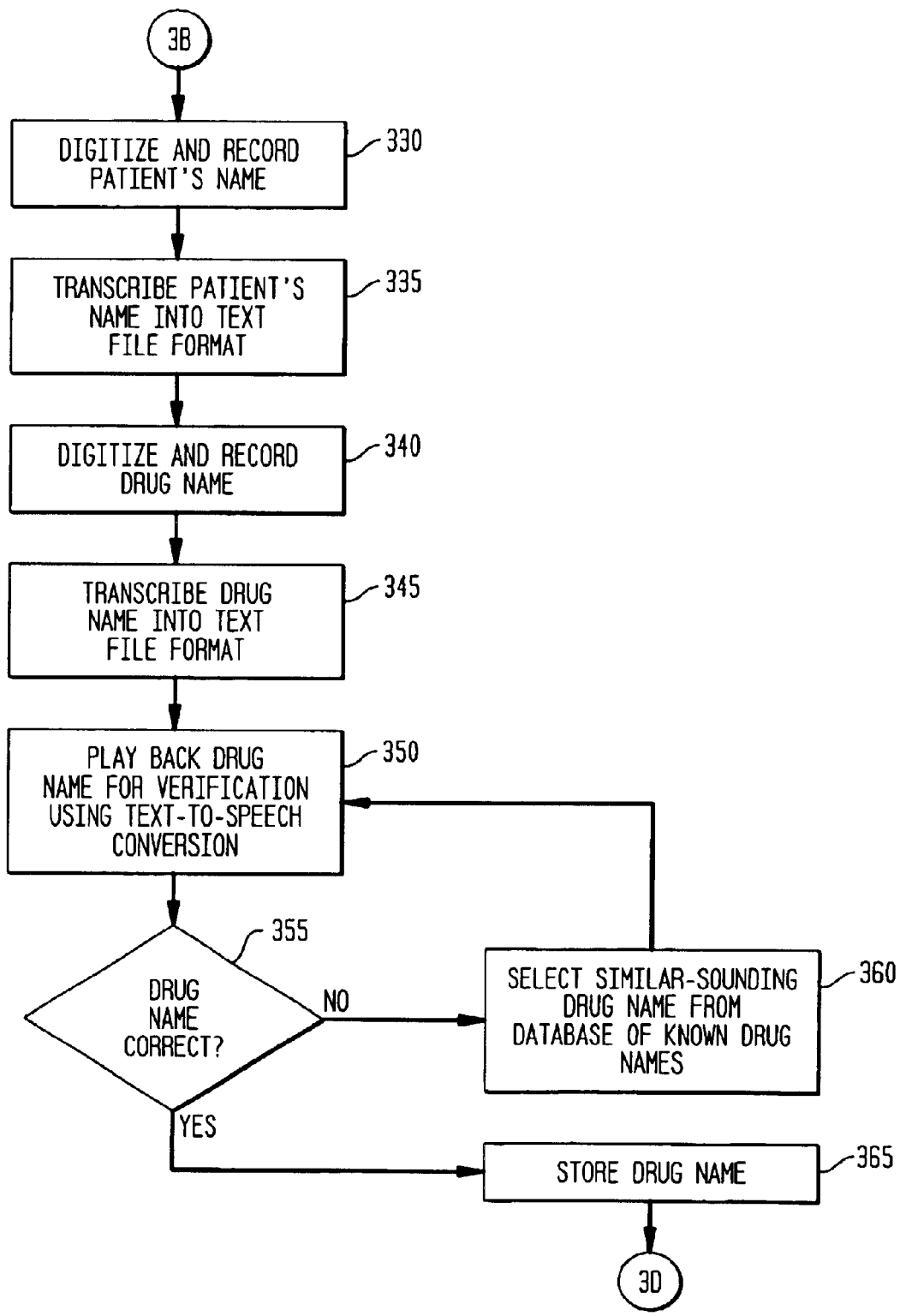

FIG. 3c is a flowchart showing additional processing logic of the present invention. Beginning in step 330, the caller is prompted to provide a patient's name. The system then digitizes and records the name in a sound file format known in the art, such as a .WAV file. Optionally, the caller can review and/or re-record the spoken patient name. Then, in step 335, the digitized and recorded name is transcribed into a text format. In step 340, the caller is then prompted to recite the name of the drug for which a prescription is desired. The recited drug name is captured, digitized, and recorded in a sound file. Then, in step 345, the drug name is transcribed into a text format using known speech-to-text conversion processes.

In step 350, the transcribed drug name is then read back to the caller using text-to-speech conversion for purposes of verification. In step 355, the caller is then prompted to provide an indication as to whether the drug name is correct. If a negative indication is made, step 355 invokes step 360, wherein the call is provided with an audible list of similar-sounding drug names from a database of known drugs. The caller can then select the correct drug from the list, using the telephone keypad or other input means. Once selected, the drug name is played back in step 350 for verification purposes. If the caller is unable to select or verify a drug name, the system will not make any drug name transcription, and will mere record the name of the drug initially recited by the caller. In the event that a positive indication is made in step 355, processing continues in step 365, wherein the drug name is stored. Processing then continues in FIG. 3d.

Depicted in FIG. 3d is a flowchart showing additional processing steps of the present invention. When the drug name had been transcribed from a caller's spoken indication, or selected by the caller form the list of known drug names, the caller is then prompted in step 370 to speak the drug signature, i.e., directions on how to take the drug and the frequency with which to take same. Once spoken, the drug signature is then digitized, recorded, and stored in a text file format using speech-to-text conversion. Then, in step 375, the stored drug signature is played back for verification purposes using text-to-speech conversion. In step 380, the caller is prompted to indicate, using the telephone keypad or other input means, whether the drug signature is correct. If a negative indication is made, step 380 re-invokes step 370, wherein the caller is prompted to again speak the drug signature for digitization, recording, storage, and re-verification. Optionally, a caller can be prompted with a selection of matching drug signatures stored in a database, and asked to select one of the signatures by pressing a corresponding button on the keypad of a telephone. If a positive indication is made, step 380 invokes step 385.

When step 385 is invoked, all information pertaining to a given prescription has been acquired by the caller, and stored in the prescription services system 10 of the present invention as sound files (e.g., .WAV, .MP3, .AU, etc.), and as transcribed text files. It is to be understood that additional information pertaining to prescriptions or other medical information can be acquired by the prescription services system 10 in the manner disclosed herein. In a preferred embodiment, the transcribed text files and audio files are stored in storage system 140 of the prescription services system 10 for quick retrieval and manipulation by the server 100, under the direction of the server itself (i.e., system maintenance and DBMS housekeeping processes performed by automated scripts and/or daemons), or under the direction of external commands received by PSTN interface 115, CSU/DSU 120, network interface 125, VoIP interface 127, or other interface with prescription services system 10. Further, in a preferred embodiment, the transcribed text files and voice files stored in storage system 140 can be backed up for safekeeping by server 100 into backup system 135 on a regular basis.

In step 385, the prescription services system 10 gathers the transcribed text files stored in the system and related to a given prescription. Then, in step 390, the transcribed textual information is assembled into a text prescription, and is transmitted to a medical facility for verification via fax, e-mail, or other communication methodology, for confirmation, review, and record keeping purposes. For example, the transcribed prescription could be transmitted to computer 34 or fax machine 36 of the medical facility 30 of FIG. 1 via Internet or WAN connection 55 or PSTN connection 40. It is to be understood that additional transmission methodologies, such as wireless communication, could be used to relay the transcribed prescription to medical facility 30, or personnel associated therewith. In an exemplary embodiment, the transcribed prescription could be transmitted by server 100 of prescription services system 10 to PSTN connection 40, VoIP connection 52, or Internet or WAN connection 55 for receipt by medical facility 30 using PSTN interface 115, CSU/DSU 120, network interface 125, or VoIP interface 127.

Once the transcribed prescription has been sent to a medical facility using any of a variety of transmission methodologies, the transcribed information can then be converted to Hypertext Markup Language (HTML), Extensible Markup Language (XML) or Electronic Data Interchange (EDI) formats by the prescription services system 10 in step 395. Once converted, the data can then be transmitted to a pharmacy for review and further processing in step 400. For example, the HTML, XML, or EDI files and messages could be sent by prescription services system 10 to computer 24, pharmacy management system 26, or central pharmacy management system 27 of the pharmacy 20 of FIG. 1 via PSTN connection 40 and/or Internet or WAN connection 45. In an exemplary embodiment, the transcribed prescription could be received as a facsimile by fax machine 22, an e-mail message or XML page by computer 24, or integrated within a legacy database system of pharmacy management system 26 or central pharmacy management system 27 using EDI files and messages. Other transmission and integration methods are considered within the scope of the invention.

In step 405, the digitized and recorded voice files are stored within prescription services system 10 for later retrieval and review by medical or pharmacy personnel. Importantly, the prescription transcription, assemblage, and transmission processes disclosed in steps 385 through 405 can be initiated by the prescription services system 10 at any desired time. For example, a systems administrator can direct the prescription services system 10 to dispatch all transcribed prescriptions to pharmacies or medical facilities in a batch run that could execute under the direction of a daemon or script at a given time each day. Further, the system could be directed to transcribe and transmit prescription immediately upon the completion of a call.

Having thus described the invention in detail, it is to be understood that the foregoing description is not intended to limit the spirit and scope thereof. What is desired to be protected by Letters Patent is set forth in the appended claims.

What is claimed is:

1. A prescription services system for transcribing and dispatching spoken prescriptions comprising:
a server remote from a caller;
a communications interface at the server for receiving a telephone call from a caller;
voice recognition software on the remote server for transcribing prescription information provided by the caller into transcribed prescriptions;
means for storing the transcribed prescriptions and at the remote server; and
means for dispatching the transcribed prescriptions to a recipient remote from the server.

2. The system of claim 1, wherein the recipient comprises a caller or a pharmacy.

3. The system of claim 1, further comprising call forwarding means for forwarding a caller from a telephone number corresponding to a pharmacy to the prescription services system.

4. The system of claim 1, wherein the means for dispatching comprises a telephonic interface for faxing the transcribed prescriptions to the recipient.

5. The system of claim 1, wherein the means for dispatching comprises a network interface for transmitting the transcribed prescriptions to a computer system located at the recipient.

6. The system of claim 5, wherein the computer system comprises a pharmacy management system.

7. The system of claim 6, wherein the prescription services system is linked to the pharmacy management system via a network connection.

8. The system of claim 1, further comprising data conversion means at the remote server for converting the transcribed prescriptions into e-mail messages for transmission to a computer system located at the recipient.

9. The system of claim 1, further comprising data conversion means at the remote server for converting the transcribed prescriptions into XML messages for transmission to a computer system located at the recipient.

10. The system of claim 1, further comprising data conversion means at the remote server for converting the transcribed prescriptions into EDI messages for transmission to a pharmacy management system located at the recipient.

11. The system of claim 1, further comprising means for storing portions of spoken prescription information in an audio file at the remote central server.

12. The system of claim 11, further comprising means for dispatching the audio file to a recipient.

13. A method for providing prescription services using voice recognition comprising:
receiving at a central server remote from a caller a telephone call relating to a prescription request;

acquiring spoken prescription information from the caller at the remote central server;

transcribing at the remote central server the spoken prescription information into a transcribed prescription using voice recognition software;

storing the transcribed prescription information at the remote central server; and dispatching the transcribed prescription to a recipient remote from the central server.

14. The method of claim 13, wherein the step of receiving a telephone call further comprises:

receiving a telephone call at a telephone number corresponding to a pharmacy; and forwarding the call to the remote central server for acquiring the spoken prescription information.

15. The method of claim 14, wherein the step of receiving a telephone call comprises receiving a Voice-Over-IP (VoIP) call at a number corresponding to the pharmacy.

16. The method of claim 13, further comprising allowing a caller to review the transcribed prescription in a subsequent telephone call.

17. The method of claim 13, wherein the step of dispatching the transcribed prescription comprises faxing the transcribed prescription to a pharmacy for filling.

18. The method of claim 13, wherein the step of dispatching the transcribed prescription further comprises faxing the transcribed prescription to the caller for confirmation.

19. The method of claim 13, further comprising converting the transcribed prescription into an e-mail message, an XML page, an HTML page, or an EDI message.

20. The method of claim 19, further comprising transmitting the e-mail message, the XML page, or the HTML page to a computer in a pharmacy for processing a prescription.

21. The method of claim 19, further comprising transmitting the e-mail message, the XML page, or the HTML page to computer located at a caller for reviewing and confirming a prescription.

22. The method of claim 19, further comprising transmitting the EDI message to a pharmacy management system at a pharmacy for processing a prescription.

23. The method of claim 13, further comprising:

connecting a pharmacy management system to the remote central server using a network connection; and allowing a pharmacist to interact with the remote central server using the pharmacy management system.

24. The method of claim 23, wherein the step of connecting the pharmacy management system to the remote central server comprises using the Internet or a network connection.

25. The method of claim 23, wherein the step of allowing the pharmacist to interact with the remote central server comprises allowing the pharmacist to access the transcribed prescriptions and spoken prescription information stored in the prescription services system using the pharmacy management system.

26. The method of claim 13, further comprising:

connecting a computer located at a caller to the remote central server; and allowing the caller to interact with the remote central server using the computer.

27. The method of claim 26, wherein the step of connecting the computer to the remote central server comprises using the Internet or a network connection.

28. The method of claim 26, wherein the step of allowing the recipient to interact with the remote central server comprises allowing the recipient to access the transcribed prescriptions and voice prescription information stored at the remote central server using the computer.

29. The method of claim 13, further comprising transcribing portions of the spoken prescription information into a transcribed prescription and storing the transcribed prescription on the remote central server, and storing portions of the spoken prescription information as an audio file and storing the audio file on the remote central server.

30. The method of claim 29, further comprising dispatching the transcribed prescription and the audio file to a recipient remote from the central server.

31. The method of claim 29, further comprising allowing a caller to review the transcribed prescription and the audio file during a call.

32. The method of claim 29, further comprising allowing a caller to review the transcribed prescription and the audio file in a subsequent call.

33. The method of claim 13, further comprising allowing a caller to review the transcribed prescription during the telephone call.

34. A method for providing prescription services using voice recognition comprising:

allowing a caller to telephone a central server at a location remote from the caller;

prompting the caller with at least one audible menu regarding prescription information;

allowing the caller to speak the prescription information in response to the at least one audible menu;

transcribing the prescription information at the central server using voice recognition techniques; and dispatching transcribed prescriptions to a pharmacy remote from the central server for filling.

35. The method of claim 34, wherein the step of allowing the caller to telephone the central server further comprises allowing the caller to call the central server using a PSTN connection.

36. The method of claim 34, wherein the step of allowing the caller to telephone the central server further comprises allowing the caller to call the central server using a VoIP connection.

37. The method of claim 34, wherein the step of allowing the caller to telephone the central server further comprises allowing the caller to call the central server using a telephonic connection forwarded from a telephone number corresponding to a pharmacy.

38. The method of claim 34, wherein the step of prompting the caller with at least one audible menu further comprises prompting the caller to provide a doctor's name.

39. The method of claim 38, wherein the step prompting the caller with at least one audible menu further comprises prompting the caller to provide a DEA number.

40. The method of claim 38, wherein the step prompting the caller with at least one audible menu further comprises prompting the caller to provide a doctor's telephone number.

41. The method of claim 38, wherein the step of prompting the caller with at least one audible menu further comprises prompting the caller to provide an Rx number.

42. The method of claim 38, wherein the step prompting the caller with at least one audible menu further comprises prompting the caller to provide a patient's social security number.

43. The method of claim 42, wherein the step prompting the caller with at least one audible menu further comprises prompting the caller to provide a patient's date of birth.

44. The method of claim 42, wherein the step of prompting the caller with at least one audible menu further comprises prompting the caller to provide a patient's name.

45. The method of claim 38, wherein the step prompting the caller with at least one audible menu further comprises prompting the caller to provide a drug name.

46. The method of claim 45, wherein the step prompting the caller with at least one audible menu further comprises prompting the caller to provide a drug signature.

47. The method of claim 34, wherein the step of allowing the caller to speak the prescription information comprises allowing the caller to enter the prescription information using a telephone keypad.

48. The method of claim 34, further comprising transmitting transcribed prescription information to the caller for verification.

49. The method of claim 34, wherein the step of dispatching the transcribed prescriptions to the pharmacy comprises transmitting the transcribed prescriptions to the pharmacy by facsimile.

50. The method of claim 34, wherein the step of dispatching the transcribed prescriptions to the pharmacy comprises transmitting the transcribed prescriptions to the pharmacy by e-mail.

51. The method of claim 34, further comprising allowing the caller to review the prescription information prior to transcribing the prescription information.

52. The method of claim 34, further comprising allowing the caller to review the prescription information in a subsequent telephone call.

53. The method of claim 34, wherein the step of dispatching the transcribed prescriptions to the pharmacy comprises transmitting the transcribed prescriptions to the pharmacy using an XML file.

54. The method of claim 34, wherein the step of dispatching the transcribed prescriptions to the pharmacy comprises transmitting the transcribed prescriptions to the pharmacy using an HTML file.

55. The method of claim 34, wherein the step of dispatching the transcribed prescriptions to the pharmacy comprises transmitting the transcribed prescriptions to the pharmacy using an EDI file.

* * * * *